United States Patent [19]

Schnabel et al.

[11] Patent Number: 4,594,462
[45] Date of Patent: Jun. 10, 1986

[54] PREPARATION OF BUTANE-1,4-DIOL

[75] Inventors: Rolf Schnabel, Schifferstadt; Hans-Martin Weitz, Bad Durkheim, both of Fed. Rep. of Germany

[73] Assignee: BASF Aktiengesellschaft, Ludwigshafen, Fed. Rep. of Germany

[21] Appl. No.: 748,998

[22] Filed: Jun. 26, 1985

[30] Foreign Application Priority Data

Jun. 26, 1984 [DE] Fed. Rep. of Germany ....... 3423447

[51] Int. Cl.$^4$ ..................... C07C 29/136; C07C 31/20
[52] U.S. Cl. ..................................... 568/864; 568/868
[58] Field of Search ................................ 568/864, 868

[56] References Cited

U.S. PATENT DOCUMENTS 4,032,458  6/1977  Cooley et al. ............... 568/864
4,032,583  6/1977  Arganbright et al. ......... 568/868
4,172,961 10/1979  Henery et al. ............... 568/864

FOREIGN PATENT DOCUMENTS 1454440 11/1976 United Kingdom .

Primary Examiner—J. E. Evans
Attorney, Agent, or Firm—John H. Shurtleff

[57] ABSTRACT

Butane-1,4-diol is prepared by catalytic hydrogenation of dibutyl succinate by a process in which hydrogenation is terminated before complete conversion is reached, butanol is distilled off from the reaction mixture, the liquid distillation residue is cooled to below 108° C., the upper phase, which is formed as a result of phase separation and essentially consists of dibutyl succinate, is recycled to the hydrogenation, and the butane-1,4-diol is obtained from the lower phase, which essentially consists of this compound, by fractional distillation under reduced pressure.

6 Claims, 1 Drawing Figure

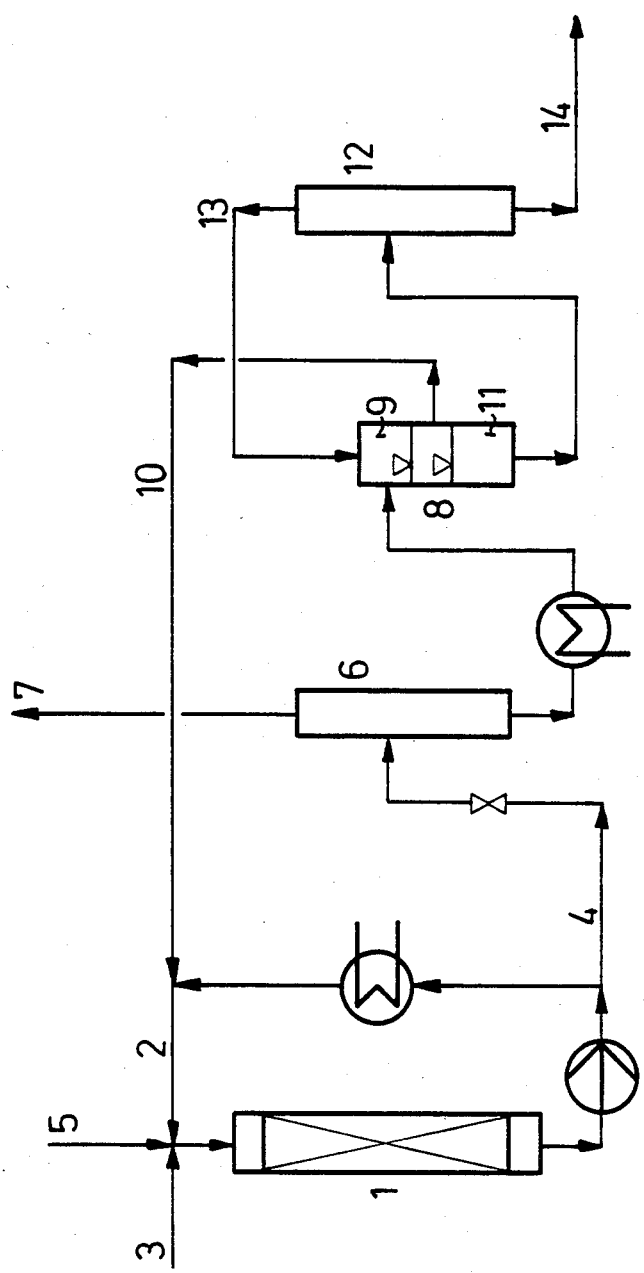

PREPARATION OF BUTANE-1,4-DIOL

The present invention relates to a process for the preparation of butane-1,4-diol by catalytic hydrogenation of dibutyl succinate.

It is known that butane-1,4-diol can be prepared by hydrogenolysis of dibutyl succinate. In this process, which is described in, for example, German Laid-Open Application DOS No. 2,543,673, the dibutyl succinate is hydrogenated in the presence of a copper chromite catalyst under a hydrogen pressure of from 100 to 300 bar and at from 200° to 260° C. The diol is isolated from the resulting mixture of butane-1,4-diol and butanol, while the butanol is reused for esterifying the maleic anhydride employed as the starting compound. In a similar process described in U.S. Pat. No. 4,032,458, the butanol is distilled off from the hydrogenation mixture. Water is added to the residue, which contains the crude butane-1,4-diol, impurities are extracted from the aqueous butane-1,4-diol by treatment with liquid hydrocarbons, and the pure butane-1,4-diol is obtained by distilling the aqueous solution treated in this manner.

In the catalytic hydrogenation of dibutyl succinate, the reaction rates have frequently found to be so low that only a relatively small amount of butane-1,4-diol is formed per space and time unit. The implication of this disadvantage is that large and correspondingly expensive plants, and substantial amounts of catalyst, are required in industrial use.

It is an object of the present invention to improve the space-time yields in the stated process.

We have found that this object is achieved, and that particularly advantageous results and in particular fairly high space-time yields are obtained in the preparation of butane-1,4-diol by catalytic hydrogenation of dibutyl succinate at from 150° to 300° C. and under pressures of above 100 bar, if hydrogenation is terminated before complete conversion is reached, butanol is distilled off from the reaction mixture, the liquid distillation residue is cooled to below 108° C., the upper phase, which is formed as a result of phase separation and essentially consists of dibutyl succinate, is recycled to the hydrogenation, and the butane-1,4-diol is obtained from the lower phase, which essentially consists of this compound, by fractional distillation under reduced pressure.

In the novel process, the dibutyl succinate is hydrogenated in a conventional manner in the presence of a hydrogenation catalyst at from 150° to 300° C., in particular from 170° to 190° C., and under a pressure of above 100, in particular from 200 to 300, bar, copper-containing catalysts preferably being used and the hydrogenation being carried out continuously by the conventional recycle procedure (see Example). According to the invention, hydrogenation is terminated before complete conversion is reached, i.e. hydrogenation is continued only to a conversion of not more than 97%, preferably not more than 90%. The resulting reaction mixtures are composed of from 91.7 to 2.9% by weight of dibutyl succinate,
from 5.2 to 60.4% by weight of butanol and
from 3.1 to 36.7% by weight of butane-1,4-diol, preferably from 49.1 to 9.7% by weight of dibutyl succinate,
from 31.6 to 56.2% by weight of butanol and
from 19.2 to 34.1% by weight of butane-1,4-diol.

Butanol is distilled off from these reaction mixtures. Distillation is advantageously carried out under atmospheric or slightly reduced pressure in a column, at a bottom temperature of, for example, from 125° to 220° C. and a top temperature of from 108° to 120° C., the distillate obtained containing butanol as the principal component. The butanol content of the liquid bottom product should fall to below 3% by weight. The liquid distillation residue is then cooled to below 108° C., whereupon phase separation takes place to give two liquid phases, the upper phase essentially consisting of unconverted dibutyl succinate, and the lower phase essentially comprising butane-1,4-diol. The upper phase is recycled to the hydrogenation and is advantageously used as a cooling medium for the recycle stream. Butane-1,4-diol is obtained from the lower phase by fractional distillation under reduced pressure. Distillation is carried out, for example, in a column under from 20 to 26 mbar, at a bottom temperature of from 146° to 152° C. and a top temperature of from 100° to 127° C. This procedure gives light ends which consist of two phases and contain virtually the total amount of dibutyl succinate, and which advantageously are recycled to the phase separator described above, while butane-1,4-diol is obtained as the main fraction.

In the process according to the invention, butane-1,4-diol is obtained from dibutyl succinate in a particularly advantageous manner and in a high space-time yield. The fact that the butane-1,4-diol can be isolated from the reaction mixture with relatively little expense by the novel process is surprising, since a procedure which has incomplete conversion as a precondition would have been expected to entail the additional expense of a distillation for separating the reaction mixture. However, the actual cost of distillation is unexpectedly low, and it has been found that, particularly surprisingly, residual dibutyl succinate can be separated off from the butane-1,4-diol in the form of a heteroazeotrope with butanediol, as light ends of a simple distillation under reduced pressure.

EXAMPLE (See FIGURE)

The following abbreviations are used:
BSBE = dibutyl succinate
BuOH = butanol
BA = butane-1,4-diol In a reactor (1) having dimensions of 111 × 8000 mm, 8 tons of BSBE were hydrogenated in a continuous experiment at 180° C. and under a hydrogen pressure of 250 bar. The reactor contained 51 l of a fixed-bed catalyst which consisted of 60% by weight of Cu and 40% by weight of $SiO_2$ and was in the form of 5 × 5 mm tablets. The reactor was incorporated in a liquid and gas circulation (2) through which 350 l/h of liquid and 60 m³ (S.T.P.) l/h of hydrogen under 250 bar flowed. 45 l/h of BSBE were fed (3) into the liquid circulation, while the corresponding amount of liquid reaction mixture was removed from it (4). Hydrogen consumed by the reaction was replaced continuously (5) via a pressure-regulating unit. The temperature at the reactor inlet (top) was 163° C., while that at the reactor outlet (bottom) was 182° C. Gas chromatographic analysis of the liquid reaction mixture removed from the reactor showed that this mixture contained 30% by weight of BA, 54% by weight of BuOH and 14% by weight of BSBE. The conversion was therefore 86%, and the space-time yield 0.26 kg of BA per l per h.

1.6 kg of the liquid reaction mixture removed from the reactor were passed into a distillation apparatus (6) comprising a 10 cm Vigreux column and a distillation bridge with a Liebig condenser. Distillation under atmospheric pressure and at bottom temperatures of from 125° to 216° C. and top temperatures of from 108° to 118° C. gave 0.87 kg of distillate (7) which contained BuOH as the main component and, according to gas chromatographic analysis, <0.1% by weight of BA and 0.1% by weight of BSBE.

The liquid bottom product was cooled to 25° C. in a separator (8), whereupon phase separation took place. The upper phase (9; 0.19 kg) contained 1.2% by weight of BuOH, 3.5% by weight of BA and 91% by weight of BSBE according to gas chromatographic analysis, and was recycled (10) to the hydrogenation. The lower BA phase (11; 0.54 kg) contained 2.7% by weight of BuOH, 83% by weight of BA and 8.0% by weight of BSBE according to gas chromatographic analysis.

The lower phase was separated off and distilled in column (12) under a pressure of from 20 to 26 mbar and at bottom temperatures of from 146° to 152° C. and top temperatures of from 100° to 127° C. to give 0.15 kg of light ends (13) which consisted of two phases and contained virtually the entire amount of BSBE. The main fraction (14) which was obtained under 20 mbar and at bottom temperatures of from 152° to 225° C. and at top temperatures of from 127° to 128° C. and essentially consisted of BA, contained less than 0.2% by weight of BSBE.

We claim:

1. A process for the preparation of butane-1,4-diol by catalytic hydrogenation of dibutyl succinate at from 150° to 300° C. and under a pressure of above 100 bar, wherein hydrogenation is terminated before complete conversion is reached, butanol is distilled off from the reaction mixture, the liquid distillation residue is cooled to below 108° C., the upper phase, which is formed as a result of phase separation and essentially consists of dibutyl succinate, is recycled to the hydrogenation, and the butane-1,4-diol is obtained from the lower phase, which essentially consists of this compound, by fractional distillation under reduced pressure.

2. A process as claimed in claim 1, wherein the dibutyl succinate is hydrogenated until the conversion is not more than 97%.

3. A process as claimed in claim 1, wherein the dibutyl succinate is hydrogenated until the conversion is not more than 90%.

4. A process as claimed in claim 1, wherein the dibutyl succinate is hydrogenated over a copper-containing catalyst at from 170° to 190° C. and under from 200 to 300 bar.

5. A process as claimed in claim 1, wherein butanol is distilled off from the reaction mixture in a column at a bottom temperature of from 125° to 220° C. and a top temperature of from 108° to 120° C.

6. A process as claimed in claim 1, wherein the butane-1,4-diol is obtained as the main fraction by subjecting the lower phase obtained as a result of phase separation to fractional distillation in a column under from 20 to 26 mbar and at a bottom temperature of from 146° to 152° C. and a top temperature of from 100° to 127° C.

* * * * *